United States Patent
Rieb et al.

[11] Patent Number: 6,015,407
[45] Date of Patent: Jan. 18, 2000

[54] COMBINATION LINEAR ABLATION AND COOLED TIP RF CATHETERS

[75] Inventors: Dale Rieb, Sunnyvale; Lorna Fosse, San Jose; Mark L. Pomeranz, Los Gatos, all of Calif.

[73] Assignee: Cardiac Pathways Corporation, Sunnyvale, Calif.

[21] Appl. No.: 09/049,332

[22] Filed: Mar. 27, 1998

Related U.S. Application Data

[63] Continuation of application No. 08/611,656, Mar. 6, 1996, Pat. No. 5,800,482.

[51] Int. Cl.[7] .................................................. A61B 17/39
[52] U.S. Cl. ............................ 606/41; 607/101; 607/105
[58] Field of Search ................................ 606/41, 42, 45, 606/46, 48–50; 600/374; 607/100–105, 122

[56] References Cited

U.S. PATENT DOCUMENTS

| | | |
|---|---|---|
| 3,044,836 | 7/1962 | Conlon . |
| 4,850,351 | 7/1989 | Herman, et al. . |
| 4,945,912 | 8/1990 | Langberg . |
| 4,979,948 | 12/1990 | Geddes et al. . |
| 5,191,883 | 3/1993 | Lennox et al. . |
| 5,230,349 | 7/1993 | Langberg . |
| 5,234,004 | 8/1993 | Hascoet et al. . |
| 5,236,413 | 8/1993 | Feiring . |
| 5,281,213 | 1/1994 | Milder et al. . |
| 5,334,193 | 8/1994 | Nardella . |
| 5,342,357 | 8/1994 | Nardella . |
| 5,348,554 | 9/1994 | Imran et al. . |
| 5,368,597 | 11/1994 | Pagedas . |
| 5,383,876 | 1/1995 | Nardella . |
| 5,423,811 | 6/1995 | Imran et al. . |
| 5,443,470 | 8/1995 | Stern et al. . |
| 5,454,370 | 10/1995 | Avitall . |
| 5,487,385 | 1/1996 | Avitall . |
| 5,505,730 | 4/1996 | Edwards . |
| 5,569,241 | 10/1996 | Edwards . |
| 5,584,872 | 12/1996 | LaFontaine et al. . |
| 5,626,136 | 5/1997 | Webster, Jr. . |
| 5,676,693 | 10/1997 | LaFontaine . |
| 5,687,723 | 11/1997 | Avitall . |
| 5,702,438 | 12/1997 | Avitall . |
| 5,879,348 | 3/1999 | Owens et al. . |
| 5,891,136 | 4/1999 | McGee et al. . |

FOREIGN PATENT DOCUMENTS

| | | |
|---|---|---|
| 0 499 491 A2 | 8/1992 | European Pat. Off. . |
| 0 539 125 A1 | 4/1993 | European Pat. Off. . |
| 1690786 A1 | 11/1991 | U.S.S.R. . |
| WO 90/07909 | 7/1990 | WIPO . |
| Wo 94/08519 | 4/1994 | WIPO . |
| WO 95/15115 | 6/1995 | WIPO . |
| WO 95/34346 | 12/1995 | WIPO . |
| WO 96/00041 | 1/1996 | WIPO . |
| WO 96/00042 | 1/1996 | WIPO . |

OTHER PUBLICATIONS

Borggrefe, et al., "High Frequency Alternating Current Ablation of an Accessory Pathway in Humans," JACC 10 (3), pp. 576–582 (1987).

Primary Examiner—Michael Peffley
Attorney, Agent, or Firm—Limbach & Limbach L.L.P.

[57] ABSTRACT

An apparatus for ablating body tissue is provided that is particularly adapted for creating both linear and point lesions in the endocardium. The apparatus comprises an elongate tubular member having a tip electrode and an ablation section mounted thereon. The ablation section includes one or more spaced electrodes, a fluid permeable foam material, and a fluid impermeable covering having a plurality of holes formed in it. The flow of conductive fluid to the ablation section during use allows contact to be maintained between the electrodes and the tissue to be ablated so as to minimize the formation of lesion breaks. The conductive fluid also serves to cool the tip electrode during its use by delivering the fluid to the tip electrode before routing it to the ablation section. In preferred embodiments, use of a shape wire and/or one or more pullwires allows the inventive apparatus to be more easily manipulated during the ablation procedure.

33 Claims, 4 Drawing Sheets

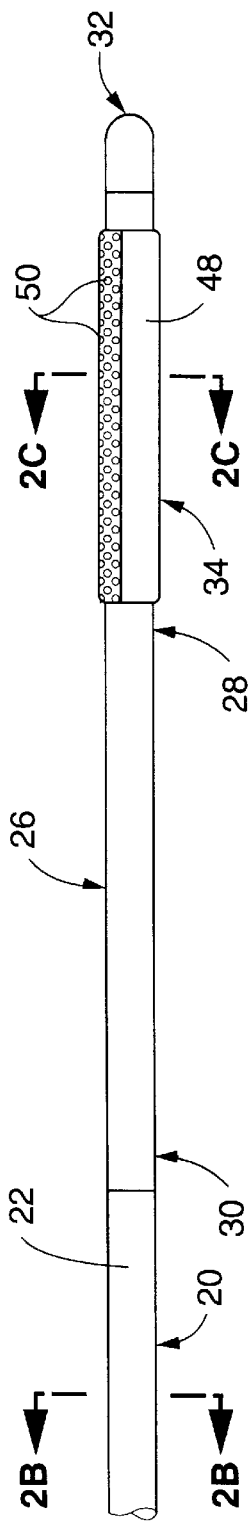
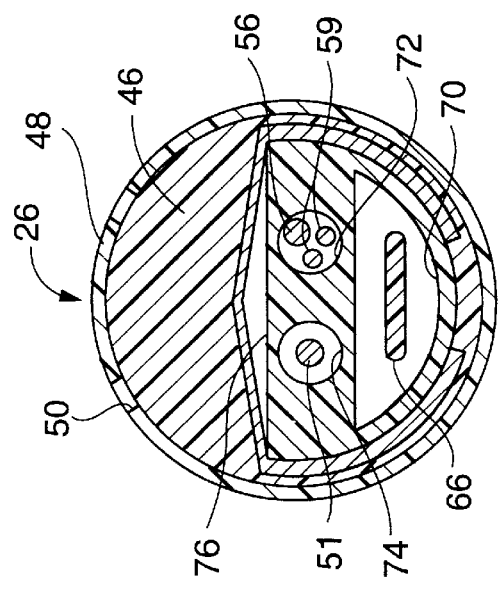
FIG. 2C
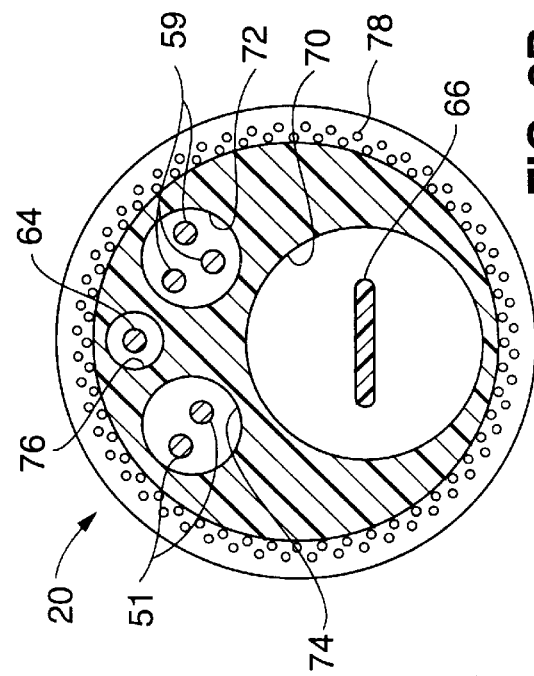
FIG. 2B
FIG. 2A

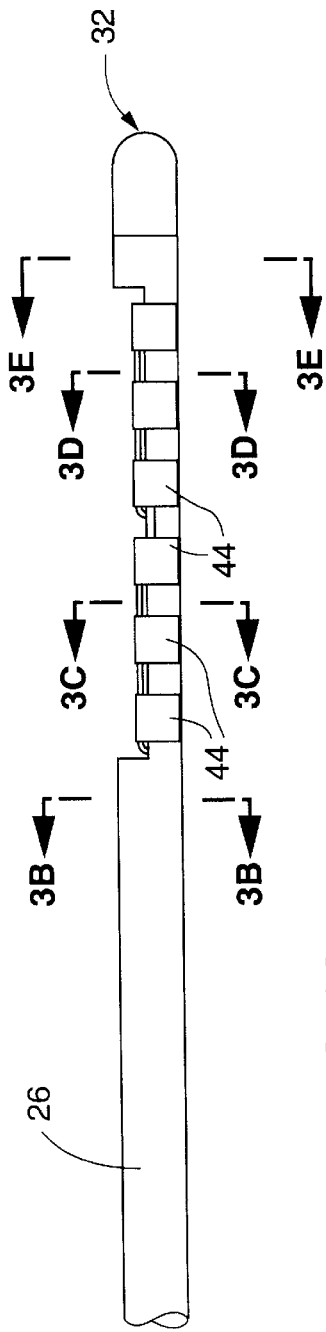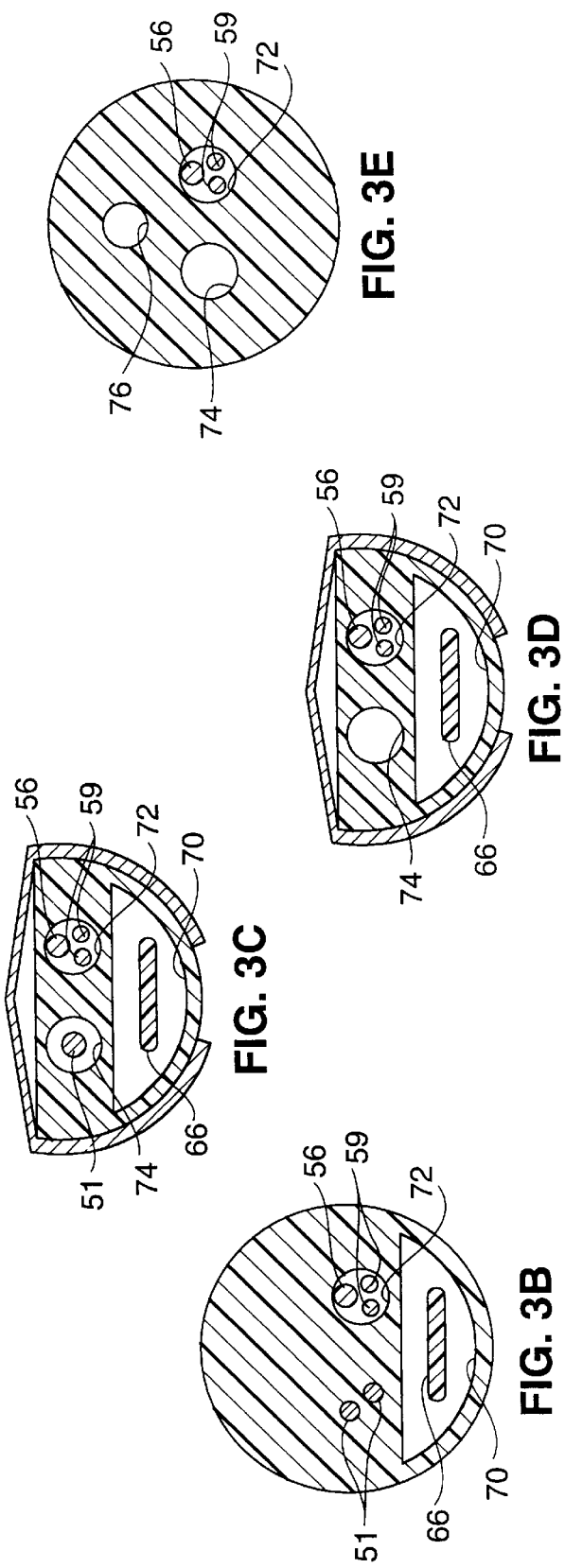

COMBINATION LINEAR ABLATION AND COOLED TIP RF CATHETERS

This is a continuation in part of application Ser. No. 08/611,656, filed Mar. 6, 1996, now U.S. Pat. No. 5,800,482, Issued Sep. 1. 1998.

BACKGROUND

The present invention generally relates to medical devices and methods for ablating living tissue. More particularly, the present invention relates to radio frequency ("RF") ablation catheters and methods for using the same to create lesions within the heart.

Atrial fibrillation is a condition in the heart in which abnormal electrical signals are generated in the endocardial tissue to cause irregular beatings of the heart. A proven protocol for successfully treating this condition is open heart surgery (sometimes referred to as the "maze" procedure) where several long (i.e. approximately 2–10 cm) lesions are created in the endocardium within the upper chambers of the heart ("atria"). These lesions block the flow of excess electrical impulses within the atria and allow the impulse from the sinus node to properly regulate heart contraction.

However, because open heart surgery is highly invasive and requires a lengthy patient recovery period, alternative methods for making lesions have been recently explored. One such alternative is the use of ablation catheters that includes one or more electrodes.

Typically, an ablation catheter is advanced into the heart via the patient's vessels. When the electrodes are placed in the desired position within the heart chamber, radio frequency ("RF") energy is supplied to the catheter thereby burning lesions into the endocardium.

Initial designs for ablation catheters generally comprised of an elongated shaft in which an electrode is mounted onto its distal end. Either point and linear lesions could be formed with these catheters by manipulating the placement of the tip. However, because of the tendency for the tip electrode to overheat and to lift off the tissue surface during ablation, creating suitable lesions using these catheters have been difficult.

New catheter designs attempted to mitigate these disadvantages. One improvement is the addition of a mechanism to cool the tip electrode during use to minimize the risk of embolism from overheated blood. Such cooled tip ablation catheters are described in U.S. Pat. Nos. 5,423,811 and 5,545,161 both of which are incorporated in their entireties herein by reference. Although these catheters mitigate the overheating problem, the tendency for the tip electrode to form uneven linear lesions still remains.

Another improvement is the substitution of the tip electrode for a series of electrodes to form a linear ablation section on the catheter. Illustrative examples of such ablation catheters are described in pending U.S. application Ser. No. 08/965,353 filed Nov. 6, 1997, now U.S. Pat. No. 5,895,417 entitled "DEFLECTABLE LOOP DESIGN FOR A LINEAR LESION ABLATION APPARATUS" by inventors Mark L. Pomeranz, Troy J. Chapman, Scott Tedder, Darren R. Sherman, and Steven C. Anderson, pending U.S. application Ser. No. 08/680,426 filed on Jul. 15, 1996, now U.S. Pat. No. 5,882,346, entitled "SHAPABLE CATHETER USING EXCHANGEABLE CORE AND METHOD OF USE" by inventors Mark L. Pomeranz and Peter Park, and allowed U.S. application Ser. No. 08/611,656 filed on Mar. 6, 1996, now U.S. Pat. No. 5,800,482, entitled "APPARATUS AND METHOD FOR LINEAR LESION ABLATION" by inventors Mark L. Pomeranz, Troy J. Chapman, Darren R. Sherman, and Mir Imran all of which are also incorporated in their entireties herein by reference.

These catheters facilitate the formation of suitable linear lesions by providing additional surface area for distributing RF energy. Although linear lesion catheters are a significant improvement over tip electrode catheters, breaks still occasionally occur due to the difficulty in maintaining sufficient contact between the ablation section and the tissue surface.

The impact of these breaks may be generally mitigated by forming point lesions at these sites in a follow up procedure. However, since linear ablation catheters are not generally suited to form point lesions, the follow up procedure typically requires removing the existing linear ablation catheter from the patient and substituting it for a tip electrode catheter. Because this catheter exchange may cause additional trauma to the patient as well as increase the overall length of the procedure, a need exists for an ablation catheter that combines the functionalities of both the tip electrode and the linear ablation section.

SUMMARY OF THE INVENTION

The present invention provides improved catheters for use in ablating tissue that allows for a greater degree of control in the type and quality of the lesions that may be formed. The inventive catheters comprise an elongate tubular member having a tip electrode and an ablation section mounted thereon. The ablation section includes one or more spaced electrodes, a fluid permeable foam material, and a fluid impermeable covering having a plurality of holes formed in it. Either point and linear lesions may be created by selectively and separately controlling the delivery of current to either the tip electrode or the ablation section electrodes. The flow of conductive fluid to the ablation section during use allows contact to be maintained between the electrodes and the tissue to be ablated so as to minimize the formation of breaks in the lesions. The conductive fluid also serves to cool the tip electrode during its use by delivering the fluid to the tip electrode before routing it to the ablation section. In preferred embodiments, use of a shape wire and/or one or more pullwires provide additional maneuverability.

BRIEF DESCRIPTION OF THE DRAWINGS

FIG. 2A is a more detailed view of the deflectable shaft region of the ablation catheter of FIG. 1.

FIG. 2B is a cross section of the main shaft at the designated plane B—B in FIG. 2A.

FIG. 2C is a cross section of the ablation section at the designated plane C—C in FIG. 2A.

FIG. 3A is an enlarged view of the ablation section without the foam and covering of the catheter of FIG. 1.

FIGS. 3B–3E are cross sections at their respective designations of the ablation section in FIG. 3A.

DETAILED DESCRIPTION OF THE DETAILED EMBODIMENTS

The present invention provides a combination ablation catheter that comprises a cooled tip electrode and a linear electrode region that allows an operator to have a greater degree of control in the type and quality of lesions that may be formed. The advantages of the combination ablation catheter of the present invention will be further described below.

Figure 1:
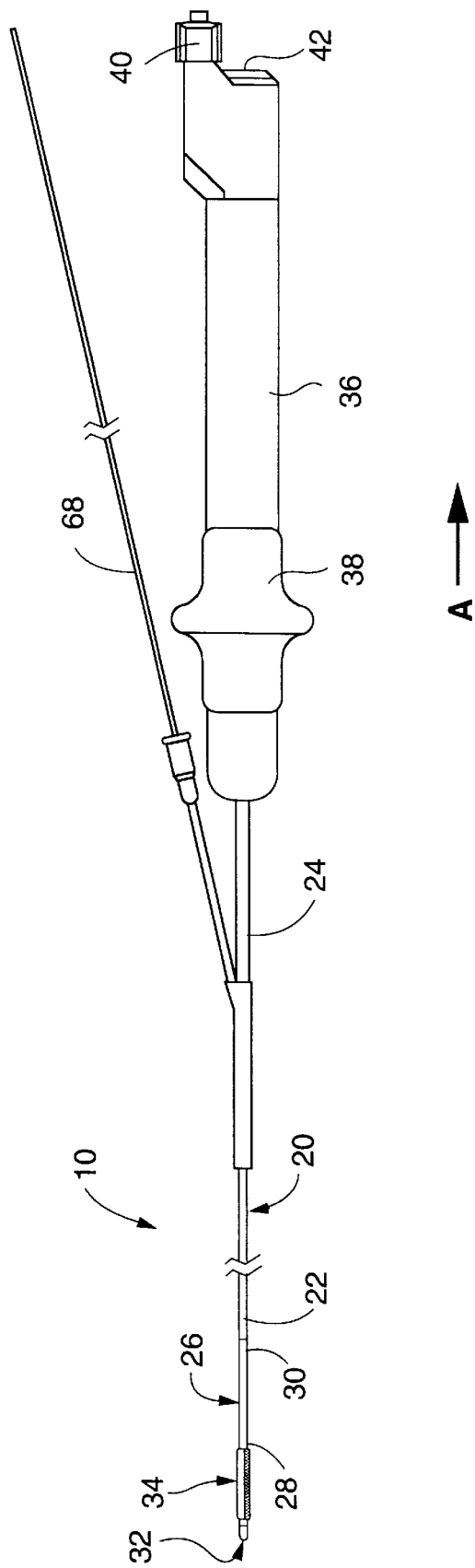
FIG. 1 is a side view of the preferred embodiment of an ablation catheter according to the present invention.

Referring to FIG. 1, inventive catheter 10 generally comprises main shaft 20 having a distal end 22 and proximal end 24; deflectable shaft 26 also having a distal end 28 and proximal end 30; tip electrode 32; and ablation section 34 mounted on to deflectable shaft 26. As depicted by FIG. 1, catheter 10 also may include handle 36 with deflection knob 38, fluid port 40, and female adapter 42 formed therein.

Proximal end 30 of deflectable shaft 26 and distal end 22 of main shaft 20 are contiguous so as to form one continuous shaft. The diameter and length of continuous shaft formed by deflectable shaft 26 and main shaft 20 may be of any suitable size that may be required for an ablation procedure. In preferred embodiments, the length of deflectable shaft 26 is between about 3 cm to about 10 cm and the diameter of both deflectable shaft 26 and main shaft 20 is between about 2 mm and 5 mm.

Both main shaft 20 and deflectable shaft 26 may be made from the same material. Suitable materials include thermoplastic polymer, polyamide ether, polyurethane and other materials having similar properties that are known in the art.

Deflectable shaft 26 differs from main shaft 20 in that it is more flexible (i.e., less rigid or stiff). This difference in flexibility allows deflectable shaft 26 to deflect to any angle between 0 to about 180° from its non-deflected state, or assume various shapes without substantially affecting main shaft 20. As it will be explained in more detail below, the change in shape of deflectable shaft 26 may be a result of actuating a pullwire or the use of a removable core wire which is formed at least in part of memory wire. In preferred embodiments, the rigidity of main shaft 20 is between about 55 and about 80 durometers and the rigidity of deflectable shaft 26 is between about 30 and about 45 durometers.

Referring to FIGS. 2 and 3, ablation section 34 is mounted on at the distal half of deflectable shaft 28 and includes one or more spaced electrodes 44, fluid permeable deformable member or foam support segment 46, and a fluid impermeable covering 48 having a plurality of holes or openings 50 formed in it. In preferred embodiments, ablation section 34 has a length of approximately between 1 cm and 5 cm and an outer diameter of approximately between 2 mm and 5 mm.

Although covering 48 may contain any number of holes in any pattern, arranging the holes along the side which will be positioned against the ablation site at a density of approximately between 20 holes/cm and 60 holes/cm is preferred. In especially preferred embodiments, covering 48 contains four rows of 0.007" diameter holes spaced 1.0 mm apart over the length of the active region of the ablation section.

Foam support segment 46 at least partially surrounds ablation section electrodes 44 and is itself enclosed within fluid impermeable covering 48 which is preferably formed of a polymeric material. Foam support segment 46 may be formed from any suitable material such as an open cell polyurethane, cotton-like material, open-cell sponge, hydrogels, or other fluid permeable compressible materials.

During use, RF energy is delivered to ablation section electrodes 44 while conductive fluid, such as saline, is simultaneously delivered to ablation section 34. The conductive fluid contacts electrodes 44 and flows out foam support segment 46 through holes 50 in covering 48. Means for delivering current and fluid to ablation section 34 will be described in detail further below.

Contact between ablation section 34 and the tissue to be ablated is enhanced in two ways. First, being deformable, foam support segment 46 can conform to the contours of the tissue to be ablated. The contact between ablation section 34 and the tissue to be ablated is further assisted by the positive pressure from the infusion of conductive fluid through foam support segment 46. Second, because the fluid is conductive, the flow of fluid serves to couple the RF energy from ablation section electrodes 44 to the tissue even if direct contact between the electrodes and the tissue is not maintained. Moreover, the conductive liquid also serves to cool ablation section electrodes 44 thus making the procedure safer by decreasing the likelihood of thrombus formation from heated blood.

Figure 4:
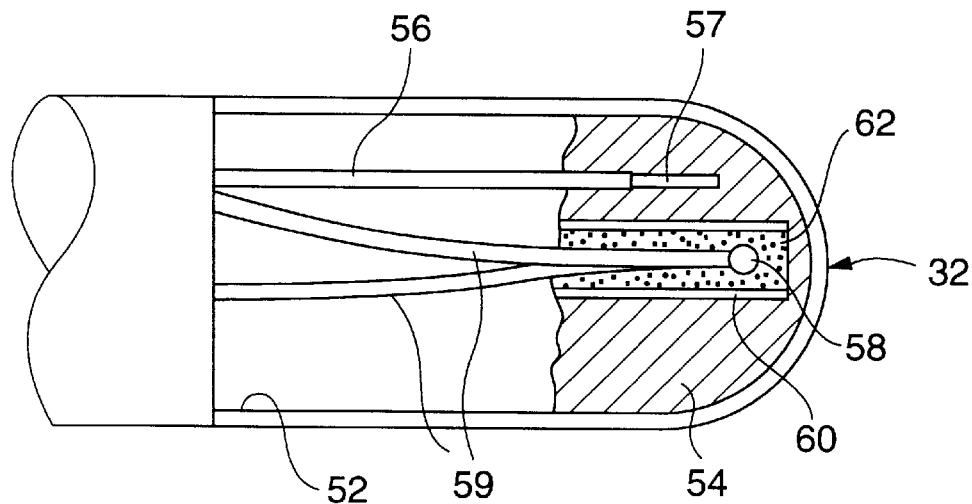
FIG. 4 is an enlarged side view of the tip electrode of the subject ablation catheter.

As shown in greater detail in FIG. 4, tip electrode 32 is attached to the most distal end 28 of deflectable shaft 26 by conventional means known in the art and includes chamber 52 formed therein. In preferred embodiments, tip electrode 32 has a rounded distal end and is between about 2 mm and 5 mm in length. As it will be further described below, tip electrode 32 is also cooled by the flow of fluid. Although tip electrode 32 may optionally include holes to allow fluid to flow therethrough as with ablation section 34, preferred embodiments deliver fluid to tip electrode chamber 52 and then remove this fluid by diverting it back through the catheter shaft in the opposite direction.

Although alternate means may be used, the internal region of the rounded distal end of tip electrode 32 is filled with conductive material 54 such as solder which acts to distribute current from lead wire 56 (via exposed wire 57) to the tip of electrode 32. A device for monitoring the temperature of tip electrode 32 may optionally be included, such as thermocouple 58 depicted in FIG. 4. However, it will be necessary to isolate thermocouple 58 from conductive material 54 by any known methods such as enclosing it in nonconductive pipe 60 filled with nonconductive adhesive 62.

Catheter maneuverability is provided by the use of one or more pullwires and/or one or more removable core wires, some of which are formed at least in part from memory or shape wire such as Nitinol. Referring back to FIG. 1, pullwire 64 (not depicted in this illustration) is attached to proximal portion (at or near end 30) of deflectable shaft 26 by conventional means and the other end is attached to deflectable knob 38 in handle 36. Alternatively, pullwire 64 may be attached within chamber 52 of tip electrode 32.

Pullwire 64 is actuated by slidably retracting deflection knob 38 along handle 36 in the direction shown by arrow A in FIG. 1. The retraction of knob 38 causes deflectable shaft 26 to be deflected. When knob 38 is moved back along handle 36 in a direction opposite arrow A, deflectable shaft 26 returns to its nondeflected state. Alternate pullwire actuation means may also be used. Although this embodiment uses only one pullwire, additional deflection points may be created by using a plurality of pullwires.

Exchangeable core wires, some of which are made at least in part of shape or memory wire, may be used either in conjunction with, or as an alternative to the one or more pullwires. Typically, only the portion of the core wire which will be carried within deflectable shaft 26 (so as to assume the desired shape) needs to be formed from memory or shape wire. As suggested by FIG. 1, core wire 66 is slidably disposed within a lumen that extends from distal end 28 of deflectable shaft 26 through the proximal portion of main shaft 20, and exits out of main shaft 20 at an opening therein. Core wire 66 preferably has a substantially flat cross-section (i.e. rectangular or oblong) to prevent the core wire from rotating about its longitudinal axis during use. In addition, means for stiffening the portion of core wire 66 which diverges from main shaft 20 is also preferred, like attaching core wire 66 to a more rigid wire 68. This facilitates the insertion and removal of core wire 66 from the catheter shaft.

During use, either a catheter without a core wire or a substantially straight core wire is used to advance the instrument through a patient's vessels. However, because of increased flexibility for threading through a patient's vessels, use of a catheter without a core wire inserted therein is generally preferred. When it is desired for deflectable shaft 26 to assume a certain shape, then an appropriate core wire that will form this shape is inserted into the catheter shaft via the opening in the proximal end 24 of main shaft 20. Removing existing core wire 66 and replacing it with one assuming a different shape may occur several times during the ablation procedure.

If both pullwire(s) and exchange core wire are to be used in the same catheter, then it is preferred that the distal ends of the pullwires all terminate in the shaft proximal to the section in deflectable shaft 26 that will assume the desired core wire shape.

Any suitable means may be used to deliver current to ablation section electrodes 44 and tip electrode 32. In preferred embodiments, current may be delivered to tip electrode 32 without also delivering current to ablation section electrodes 44 and vice versa. This is typically achieved by using a switch box linked to catheter 10 via female port 42 that allows RF energy to be directed from an RF source to either the tip electrode lead wire(s) or the ablation electrode lead wires or if desired, both. The RF source may be any conventional RF generator such as Model 8002 or 8004 RF Generator by Cardiac Pathways, Inc. (Sunnyvale, Calif.).

Similarly, any conventional means may be used to deliver conductive fluid to ablation section 34, and to deliver and remove cooling fluid to and from tip electrode 32. For the sake of efficiency, it is preferred that the conductive fluid is also used as the cooling fluid for tip electrode 32.

Although any number of lumens may be used to accomplish delivering current and fluid to the appropriate sites, minimizing the number of lumens necessary for the task is generally preferred for manufacturing expediency. In preferred embodiments, main shaft 20 and deflectable shaft 26 include four lumens therein. These lumens are illustrated in FIGS. 2B–2C and FIGS. 3B–3E.

FIG. 2B illustrates a cross section of main shaft 20. The four lumens include lumen 70 for core wire 66; lumen 72 for tip electrode lead 56 and thermocouple leads 59; lumen 74 for ablation electrode leads 51; and lumen 76 for pullwire 64. As it will be further explained below, lumen 72 is also used to deliver fluid from fluid port 40 to chamber 52 of tip electrode 32 and the distal portion of lumen 74 is used to route fluid from chamber 52 to ablation section 34.

A stainless steel braid 78 is preferably embedded in the wall of main shaft 20 by conventional means known in the art. The inclusion of the braid improves the torque characteristics of main shaft 20 and thus makes the shaft easier to maneuver through a patient's vessels and heart. To minimize the possibility for tissue trauma as the ablation catheter is fed through a patient's blood vessels and heart during use, wire braid 78 is preferably absent from deflectable shaft 26. This leaves the catheter tip sufficiently flexible to yield when advanced against obstacles within the vessels and heart.

FIG. 2C is a cross section of ablation section 34. Lumens 70, 72, and 74, and their respective contents are as previously described. Lumen 76 exists but is empty because pullwire 64 terminated at some point within the proximal portion of deflectable shaft 26.

However, as previously described, if the pullwire terminated within chamber 52 of tip electrode 32 instead of the proximal portion of deflectable shaft 26 then pullwire 64 would be present in lumen 76. Additionally, FIG. 2C shows foam support segment 46 and fluid impermeable covering 48.

FIGS. 3B–3E are additional cross sections of ablation section 34 which serve to illustrate the preferred coupling between the means for cooling tip electrode 32 and the means for delivering conductive fluid to ablation section 34. As described previously, lumen 72 delivers fluid from fluid port 40 to chamber 52 of tip electrode 32 (as well as carry tip electrode lead 56 and thermocouple lead 59).

FIG. 3E is a cross section which is closest to tip electrode 32. Lumen 70 carrying core wire 66 is not seen since it terminated at a position proximal to this cross section. Lumen 74 which carries ablation section electrode leads 51 is empty since the leads terminated previously at their respective electrodes.

Figure 5:
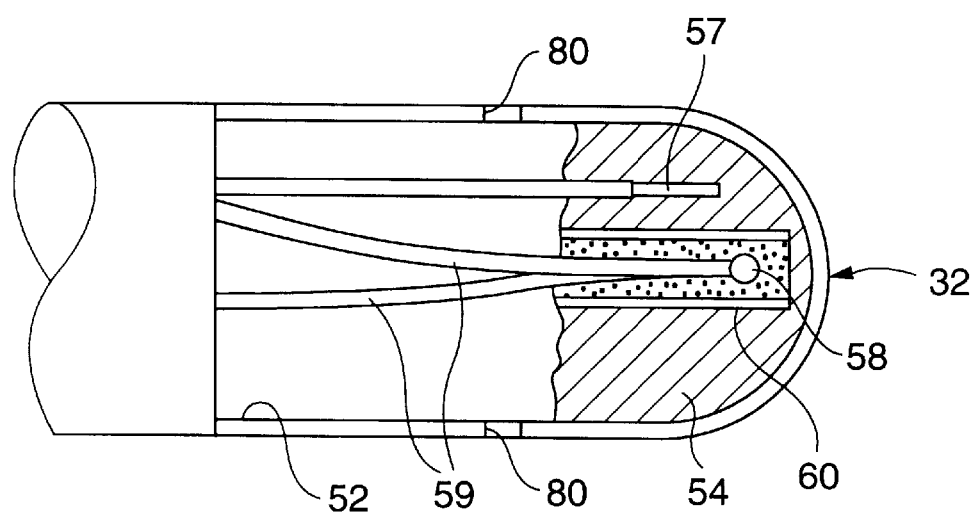
FIG. 5 is an alternative embodiment of the tip electrode.

Conductive cooling fluid is delivered to chamber 52 via lumen 72. When the fluid reaches chamber 52, fluid fills the chamber and is routed back away from tip electrode 32 through lumen 74. When an alternative embodiment for the tip electrode is used, such as that depicted by FIG. 5, then cooling fluid will also exit out from tip electrode 32 from holes 80. In either embodiments, fluid is not able to flow back through lumen 72 because of the positive pressure created by the inflowing fluid. This continuous flow of fluid results in cooling tip electrode 32 during use.

From tip electrode chamber 52, conductive fluid is routed back through the catheter shaft towards ablation section 34 via lumen 74 (which also carries ablation electrode leads 51). Openings (not depicted) in lumen 74 within ablation section 34 allows fluid to flow from lumen 74 through foam support member 46 and out holes 50 in covering 48. The flow of fluid does not continue through lumen 74 toward main shaft 20 because as depicted by FIG. 3B, lumen 74 is closed off at a point proximal to ablation section 34.

It should be understood that various features of the preferred embodiments may be used in any combination with one another. For example, catheter 10 may include only pullwire 64 and not include exchangeable core wire 66. Alternatively, the means for delivering conductive fluid to ablation section 34 may be independent from the means for delivering cooling fluid to and for removing cooling fluid from tip electrode 32.

Moreover, although the present invention has been described with reference to preferred embodiments, it should be appreciated that these embodiments are for purposes of illustration only and are not intended to limit the scope of the appended claims.

What is claimed is:

1. A catheter for ablating body tissue, comprising:

a shaft having a bendable distal section and a distal end;

a tip electrode having a chamber formed therein and attached to the distal end of the shaft;

an ablation element carried on the distal section of the shaft; and, means for delivering current to the tip electrode;

means for delivering current to the ablation element;

means for delivering fluid to the tip electrode chamber to cool the tip electrode during use; and, means for withdrawing the fluid from the tip electrode.

2. The catheter of claim 1 wherein the tip electrode include a means for measuring temperature.

3. The catheter of claim 1 wherein the means for delivering the current to the tip electrode is independent from the means for delivering the current to the ablation section such that current may be separately delivered to either the tip electrode or the ablation section electrodes.

4. The catheter of claim 1 further comprising:
a pullwire extending through the shaft member, and having a fixed distal end and a moveable proximal end for adjusting the bend of the distal end of the shaft member.

5. The catheter of claim 1 further comprising:
a fluid permeable deformable member at least partially covering the ablation element and
means for delivering conductive fluid through the deformable member.

6. The catheter of claim 5 further comprising a covering on the deformable member, the covering formed of a material substantially impermeable to fluid, the covering including at least one opening sized to allow passage of fluid out of the covering.

7. The catheter of claim 1 wherein the cooling fluid is conductive.

8. The catheter of claim 7 further comprising:
a fluid permeable deformable member at least partially covering the ablation element and wherein the means for withdrawing the fluid from the tip electrode is by delivering the fluid through the deformable member.

9. The catheter of claim 1 further comprising a core wire carried within the shaft member.

10. The catheter of claim 9 wherein the core wire is formed at least in part of memory wire and the shaft member includes an opening at its proximal end, such that the core wire is slidably disposed in and removable from the shaft member through the proximal end opening of the shaft.

11. The catheter of claim 1 wherein the tip electrode chamber includes at least one opening sized to allow fluid to exit from the tip electrode during ablation.

12. An apparatus for ablating body tissue, comprising:
an elongate tubular member having a distal end;
a tip electrode attached to the distal end of the elongated member, wherein the tip electrode includes a chamber formed therein;
an ablation section having one or more electrodes carried on the elongate tubular member;
a fluid permeable deformable member at least partially covering the ablation section electrodes;
means for delivering current to the tip electrode;
means for delivering current to the ablation section electrodes;
means for delivering cooling fluid to the tip electrode chamber wherein the cooling fluid cools the tip electrode during use;
means for withdrawing the cooling fluid from the tip electrode chamber after its use; and
means for delivering conductive fluid through the deformable member in the ablation section such that when the electrodes are placed adjacent to the body tissue, the fluid creates a conductive path between the ablation section electrodes and the tissue.

13. The apparatus of claim 12 further comprising a core wire carried within the elongate tubular member.

14. The apparatus of claim 13 wherein the core wire is formed at least in part of memory wire and the elongate tubular member includes an opening at its proximal end, such that the core wire is slidably disposed in and removable from the elongate tubular member through the proximal end opening of the elongate tubular member.

15. The apparatus of claim 12 wherein the means for delivering the current to the tip electrode is independent from the means for delivering the current to the ablation section such that current may be separately delivered to either the tip electrode or the ablation section electrodes.

16. The apparatus of claim 1 wherein the cooling fluid is also conductive and the means for delivering conductive fluid to ablation section is coupled to the means for removing cooling fluid from the tip electrode chamber.

17. The apparatus of claim 16 wherein the cooling fluid is withdrawn from the tip electrode chamber by delivering the cooling liquid through the deformable member in the ablation section.

18. The apparatus of claim 1 wherein the tip electrode chamber contains one or more openings for allowing at least some portion of the cooling liquid to exit out the tip electrode chamber while the tissue is being ablated.

19. The apparatus of claim 12 wherein the deformable member includes a layer of foam over the ablation section electrodes.

20. The apparatus of claim 19 further comprising a covering on the deformable member, the covering formed of a material substantially impermeable to fluid, the covering including at least one opening sized to allow passage of fluid out of the covering.

21. The apparatus of claim 12 wherein the tip electrode includes a means for measuring temperature.

22. The apparatus of claim 12 wherein the distal end of the elongate tubular member is bendable and wherein the apparatus further comprises:
a pullwire extending through the elongate tubular member, the pullwire having a fixed first end and a moveable second end for adjusting the bend of the distal end of the elongate tubular member.

23. The apparatus of claim 1 further comprising a plurality of pullwires, each having a distal end connected to a portion of the tubular body and a proximal end moveable to adjust the orientation of the distal portion of the tubular body.

24. A multipurpose device for ablating tissue comprising:
an elongated catheter having a fluid carrying lumen extending from the proximal to the distal end thereof;
a first electrode located at the distal tip of the catheter, the first electrode being thermodynamically coupled to fluid carried in the lumen;
a plurality of second electrodes located near but spaced apart from the distal end of the catheter, the second electrodes being covered by elongated fluid permeable material and positioned relative to the lumen so that fluid can pass out of the lumen, through the fluid permeable material and to the tissue; and
means for delivering current to the first and second electrodes.

25. A method for ablating tissue using a catheter having a tip electrode located on its distal end and a plurality of second electrodes located near but spaced apart from the tip electrode, comprising:
forming at least one linear lesion using the plurality of second electrodes by supplying RF energy and conductive fluid to the electrodes, and permitting the conductive fluid to form a conductive path between the electrodes and the tissue which is to be ablated and then forming at least one point lesion using the tip electrode.

26. The method as in claim 25 wherein the point lesion is formed in the same site as the linear lesion.

27. A method for ablating tissue using a catheter having a tip electrode located on its distal end and a plurality of second electrodes located near but spaced apart from the tip electrode, comprising:

forming at least one point lesion using the tip electrode and then forming at least one linear lesion using the plurality of second electrodes by supplying RF energy and conductive fluid to the electrodes, and permitting the conductive fluid to form a conductive path between the electrodes and the tissue which is to be ablated.

28. An apparatus for ablating body tissue, comprising:

an elongate tubular member having a distal end;

a tip electrode attached to the distal end of the elongated member and having a chamber formed therein, said electrode connectable to a source of ablation energy;

an ablation section having one or more electrodes carried on the elongate tubular member, said one or more electrodes connectable to a source of ablation energy;

a fluid permeable deformable member at least partially covering the ablation section electrodes;

a source of conductive fluid fluidly coupled for delivery through the deformable member in the ablation section such that when the electrodes are placed adjacent to the body tissue, the fluid creates a conductive path between the ablation section electrodes and the tissue; and a source of cooling fluid fluidly coupled for delivery to and subsequent withdrawal from the tip electrode chamber wherein the cooling fluid cools the tip electrode during use.

29. The apparatus of claim 28 wherein the cooling fluid is also conductive and the source of conductive fluid and the source of cooling fluid are fluidly coupled to one another.

30. The apparatus of claim 29 wherein the source of conductive fluid and the source of cooling fluid are fluidly coupled such that cooling fluid withdrawn from the tip electrode is delivered through the deformable member in the ablation section.

31. The apparatus of claim 28 wherein the tip electrode chamber contains one or more openings for allowing at least some portion of the cooling liquid to exit out the tip electrode chamber while the tissue is being ablated.

32. The apparatus of claim 28 further comprising a covering on the deformable member, the covering formed of a material substantially impermeable to fluid, the covering including at least one opening sized to allow passage of fluid out of the covering.

33. The apparatus of claim 28 further including a fluid lumen extending to the distal end of the elongate tubular member, wherein the source of conductive fluid and the source of cooling fluid include the fluid lumen.

* * * * *

UNITED STATES PATENT AND TRADEMARK OFFICE
CERTIFICATE OF CORRECTION

PATENT NO. : 6,015,407
DATED : January 18, 2000
INVENTOR(S) : Dale Rieb et al.

It is certified that error appears in the above-identified patent and that said Letters Patent is hereby corrected as shown below:

<u>Column 8,</u>
Line 10, delete "section" and insert -- element --
Line 11, delete "section electrodes" and insert -- element --

Signed and Sealed this

Twenty-eighth Day of August, 2001

Attest:

*Nicholas P. Godici*

NICHOLAS P. GODICI
*Attesting Officer*     *Acting Director of the United States Patent and Trademark Office*